United States Patent [19]

Campbell et al.

[11] Patent Number: 4,832,953
[45] Date of Patent: May 23, 1989

[54] METHOD FOR PREVENTING THE FORMATION OF A CRYSTALLINE HYDRATE IN A DISPERSION OF A LIQUID IN A MONAQUEOUS MATRIX

[75] Inventors: Patricia S. Campbell, Palo Alto; David J. Enscore, Sunnyvale; Robert M. Gale, Los Altos; Arnold Kaufman, Palo Alto, all of Calif.

[73] Assignee: Alza Corporation, Palo Alto, Calif.

[21] Appl. No.: 85,052

[22] Filed: Aug. 13, 1987

[51] Int. Cl.$^4$ .............................................. A61F 13/02
[52] U.S. Cl. ..................................... 424/448; 424/449
[58] Field of Search ...................... 424/443, 448, 449; 53/440; 264/212, 235, 345; 156/85

[56] References Cited

U.S. PATENT DOCUMENTS

| | | | |
|---|---|---|---|
| 4,262,003 | 4/1981 | Urquhart et al. | 514/872 X |
| 4,436,741 | 3/1984 | Urquhart et al. | 514/946 X |
| 4,532,244 | 7/1985 | Innes | 514/953 X |
| 4,610,875 | 9/1986 | Panoz et al. | 424/80 |

*Primary Examiner*—Thurman K. Page
*Attorney, Agent, or Firm*—Steven F. Stone; Edward L. Mandell; Paul L. Sabatine

[57] ABSTRACT

A method for preventing the formation of crystalline hydrates in a dispersion of a hydratable liquid in a nonaqueous matrix is disclosed. The method is particularly useful in the manufacture of laminated items formed from such dispersions and comprises forming individual subunits from such dispersions, heating the subunits, preferably after they have been packed in sealed containers, to a temperature high enough to melt the crystalline hydrate, maintaining said subunits at such temperature for a time sufficient to melt all the crystalline hydrate present and to prevent the occurrence of crystals for an extended period of time after cooling and cooling subunits to ambient conditions. The use of the method in the manufacture of transdermal delivery devices for the delivery of scopolamine base is described.

24 Claims, No Drawings

METHOD FOR PREVENTING THE FORMATION OF A CRYSTALLINE HYDRATE IN A DISPERSION OF A LIQUID IN A MONAQUEOUS MATRIX

FIELD OF THE INVENTION

This invention relates to the formation of liquid dispersions of a hydratable liquid in a nonaqueous matrix and more particularly relates to the manufacture of delivery devices which utilize such liquid dispersions in the delivery of drugs or other biologically active agents.

BACKGROUND OF THE INVENTION

Dispersions of drugs or other biological agents in nonaqueous, typically polymeric, matrices are commonly used as reservoirs for delivery devices, representative devices being disclosed U.S. Pat. Nos. 3,598,122 and 3,598,123 to Zaffaroni et al, 4,031,894 to Urquhart et al and 4,201,211 to Chandrasekaran et al which patents are incorporated herein by reference. For convenience the term "drug" will be hereafter used in its broadest sense to include any biologically active agent which is delivered to its environment of use to produce a biological effect. The drugs may be in solid form as for example in Chandrasekaran et al or in the form of a liquid dispersion as in Urquhart et al. It is with respect to such liquid dispersions that this invention relates.

Although this invention will be described hereafter specifically with respect to scopolamine delivery devices, it should be recognized that it is applicable to dispersions of any other drug which is in a liquid state at ambient temperatures and forms a crystalline hydrate upon exposure to water. Such drugs as nicotine, secoverine and benztropine, for example, may, to the extent they form crystalline hydrates, be treated in a manner similar to the methods by which dispersions of scopolamine base are treated according to this invention.

Transdermal delivery devices for the administration of scopolamine of the type disclosed by Urquhart et al are used extensively for the prevention of motion sickness. The product is manufactured as described in the patent by solvent casting of chloroform solutions of scopolamine base in polyisobutene (PIB) and mineral oil (MO) onto impermeable webs to form drug reservoir and adhesive films. Upon evaporation of the chloroform, a dispersion of liquid scopolamine base in the PIB/MO matrix is formed. The drug reservoir and adhesive films are then laminated to opposite sides of a release rate controlling membrane, formed from a mineral oil impregnated microporous film, to produce a multilaminate comprising a removable release liner lamina, an adhesive lamina, a rate controlling membrane lamina, a drug reservoir lamina and an impermeable backing lamina. The multilaminate is then die cut into individual systems and packaged in individual heat sealed foil pouches.

The manufacture of the product in this manner was carried out for approximately five years with no indication of the formation of any crystals of scopolamine hydrate in either the drug reservoir or the adhesive. After that time, small crystals of scopolamine hydrate were observed, but this did not present a problem because the release rate of the drug from the device was not affected by the presence of the small number of small crystals then occurring.

Approximately two years later, larger numbers of rapidly propagating crystals were observed, primarily in the drug reservoir, with a lower incidence being observed in the contact adhesive layer which contained a lower concentration of scopolamine base. At that time, the size of the crystals and their frequency of occurrence had increased to the point where they produced a significant adverse effect on the release rate of scopolamine from the device. Thereafter, every lot manufactured developed unacceptably high crystal size and frequency and commercial production had to be halted until the problem could be solved.

The individual laminate films and the multilaminate films exhibited crystallization at a much lower frequency. After the multilaminate film was fed through the die-cutting machine for the formation of the individual transdermal delivery units, crystallization began around the edges of the cut product and crystalline growth thereafter propagated rapidly throughout the mass of the reservoir and in some cases the adhesive layer. Visually observable crystals were not necessarily apparent immediately after the cutting step; instead they would typically develop over a period of days. Microscopic examination detected crystals at an earlier stage, suggesting that submicroscopic nucleation sites are present at an even earlier time.

It should be noted that the above described crystallization phenomena occurred without any significant change in the manufacturing facilities, equipment or processes and, once it had occurred, it never ceased occurring. Various attempts to eliminate the problem were tried over several months, all to no avail. For example, the drug reservoir laminate, adhesive laminate an the multilaminate film were heated overnight with no observable effect. The casting solutions were similarly heated and allowed to stand for extended periods also with no effect. Because crystallization seemed to appear after the step in which the multilaminate film is cut into individual devices, cutting and packaging the systems under dry nitrogen was instituted but crystals still appeared.

Attempts were also made to remove water from other stages of the manufacturing process. The scopolamine base is produced from an aqueous solution of scopolamine hydrobromide by titration to a basic pH with sodium hydroxide and extracting the base so formed with chloroform. The chloroform solution of the scopolamine base is then admixed with the PIB and MO as described in the aforesaid Urquhart et al patent to provide the appropriate casting solutions.

To reduce the amount of residual water in the chloroform solution of the scopolamine base, the solution was dried with drying agents such as anhydrous sodium sulfate and magnesium sulfate. Crystallization still occurred. The chloroform solution was exposed to a molecular sieve material in order to remove residual water. Crystallization still occurred. Azeotropic distillation of the chloroform solution was attempted, again to no avail even though the water content was significantly reduced.

Another approach considered was to allow the casting solutions to age for up to two weeks prior to casting and to heat the solutions prior to casting up to 60° C. overnight. This too was ineffective in preventing the occurrence of the crystals.

Against this background, it was therefore totally unexpected when the process developed by the applicants was tested and found successful for the prevention of the formation of the scopolamine hydrate crystals.

It is accordingly an object of this invention to prevent the formation of crystalline hydrate in a dispersion of a hydratable liquid in a nonaqueous matrix.

It is another object of this invention to prevent formation of crystals of scopolamine hydrate in dispersions of scopolamine base in a nonaqueous matrix.

It is another object of this invention to manufacture transdermal therapeutic systems for the controlled delivery of scopolamine base which are free from crystals of scopolamine hydrate.

These and other objects of this invention will be readily apparent from the following description of the invention.

DESCRIPTION OF THE INVENTION

According to our invention, we have found that the formation of crystalline hydrates in a liquid dispersion of a hydratable liquid in a nonaqueous, typically polymeric, matrix can be prevented if, after the articles to be manufactured from the dispersion have been cut to shape and preferably after they have been placed in their packages, the articles are heated to a temperature above the melting point of the crystalline hydrate, are maintained at that temperature for a period of time and then allowed to cool to ambient conditions. We have found that when so treated, crystals initially present disappear, do not reform upon cooling to ambient conditions and have not shown signs of crystal formation after storage at ambient conditions and udder accelerated aging conditions for several months.

The temperature and time are not critical provided they are adequate to prevent tee formation of crystals after cooling and are not so high as to cause damage to either the containers or the contents thereof. If crystals are initially present, the temperature must be at, and preferably above, the melting point of the hydrate and the time should be sufficient to cause melting of all the crystals present If crystals are not present at the time of the heating step there is some indication that temperatures lower than the melting point of the hydrate may be effective. Nevertheless, it is preferable from the point of quality assurance and uniformity of processing conditions to heat above the melting point. We have found that, with respect to preventing the formation of crystals of the hydrate of scopolamine base having a melting point of 59° C., heating the units to 60° C. for 24 hours was sufficient to melt the crystals that were present and to prevent the formation of crystals after cooling. It is contemplated, however, that a lower temperature and a shorter time could still be effective according to this invention. Suitable temperatures and times for any particular system can be readily determined by workers skilled in the art.

Although this invention will be described with respect to a specific example relating to the manufacture of transdermal delivery devices for the controlled delivery of scopolamine, it should be recognized that this invention is applicable to the processing of dispersions of any liquid agent capable of forming a crystalline hydrate. Liquid agents which may have these characteristics include, without limitation, secoverine, benztropine and nicotine.

Having thus generally described our invention, the following specific example is provided.

EXAMPLE I

Scopolamine base was formed by dissolving scopolamine hydrobromide in an aqueous sodium bicarbonate sodium carbonate buffer solution. Sodium hydroxide was added until a pH of about 9.6 was reached at which point the scopolamine base precipitated from solution and was extracted with chloroform. The chloroform solution of scopolamine base was then used as the source of scopolamine in the following preparation. 20.9 parts high molecular weight PIB (sold under the designation Vistanex L-100, 1,200,000 viscosity average molecular weight), 26.1 parts low molecular weight PIB (sold under the designation Vistanex LM-MS, 35,000 viscosity average molecular weight), 41.7 parts mineral oil (10 cp at 25° C.) and 11.3 parts scopolamine base were dissolved in chloroform in a mixer and solvent cast to form a film approximately 50 micrometers dry thickness on an approximately 65 micrometer backing film of aluminized polyethylene terephthalate (sold under the designation Scotchpak®) to form, upon evaporation of the chloroform, a scopolamine base reservoir-impermeable backing laminate. The contact adhesive layer/strippable release liner laminate was similarly prepared by solvent casting onto a 75 micrometer siliconized, polyethylene terephthalate film, a 50 micrometer dry thickness adhesive layer formed from a chloroform solution of 23.1 parts of said high molecular weight polyisobutene, 28.8 parts of said low molecular weight polyisobutene, 46.1 pars of said mineral oil, and 2.0 parts of said scopolamine base. The backing-reservoir laminate and the adhesive-release liner laminate were then laminated to opposite sides of a 25 micrometer microporous polypropylene membrane (sold under the designation Celgard® 2400) saturated with mineral oil and 2.5 cm² circular disk-shaped bandages were punch-cut from the resulting five-layer laminate. The individual bandages so produced were packaged within heat-sealed foil-lined pouches. The pouches were then heated in an oven to 60° C. and held at that temperature for 24 hours and thereafter allowed to cool to ambient conditions.

Samples treated according to this invention and samples manufactured as described above without the final heating step have been monitored over periods of up to 6 months and other samples have been subjected to accelerated aging at 37° C. for like periods. To date, none of the samples treated according to this invention exhibited any crystallization, whereas the control samples not subjected to the final heating step ultimately developed scopolamine hydrate crystals which unacceptably affected the release rate. The devices produced according to this invention, however, exhibited release rates within the applicable specifications for the product. Further, the accelerated aging studies indicate that the product produced according to this invention should remain stable for at least 3 years, a typical shelf life for a product of this type.

The above described Example contained dispersions of the drug in both the reservoir and adhesive laminate because the device contained a priming dose of the drug in the adhesive. It should be recognized however that the adhesive lamina need not contain a priming dose in which case only the reservoir lamina would be a dispersion of the liquid drug, the adhesive lamina comprising a solution of the drug in the polymer matrix.

Having thus described our invention, it is readily apparent that various modifications can be made by workers skilled in the art without departing from the scope of this invention which is limited only by the following claims wherein:

We claim:

1. A method for manufacturing delivery devices for the transdermal administration of a liquid drug capable of forming a crystalline hydrate which comprises, in combination:
   a. forming a laminate, at least one lamina of which comprises a dispersion of said liquid drug in a nonaqueous matrix;
   b. cutting subunits forming said delivery devices from said laminate;
   c. packaging said delivery devices in sealed containers;
   d. heating said delivery devices in said containers to a temperature above the melting point of said crystalline hydrate and maintaining said delivery devices at such temperature for a time sufficient to prevent the formation of said crystalline hydrate for a substantial period of time after cooling of the subunits to ambient temperatures; and
   e. cooling the delivery devices to ambient conditions.

2. The method of claim 1 wherein said laminate comprises an impermeable backing lamina, a drug reservoir lamina, a release rate controlling lamina, an adhesive lamina and a release liner lamina and said dispersion forms said reservoir lamina.

3. The method of claim 2 wherein said dispersion forms said adhesive lamina.

4. A process for manufacturing delivery devices for the transdermal administration of scopolamine base which comprise in combination:
   a. forming a laminate, at least one lamina of which comprises a dispersion of said scopolamine base in a nonaqueous matrix;
   b. cutting subunits forming said delivery devices from said laminate;
   c. packaging said delivery devices in sealed containers;
   d. heating said delivery devices in said containers to a temperature above the melting point of crystalline scopolamine hydrate and maintaining said delivery devices at such temperature for a time sufficient to prevent the formation of said crystalline hydrate for a substantial period of time after cooling of the subunits to ambient temperatures; and
   e. cooling the delivery devices to ambient conditions.

5. The process of claim 4 wherein said laminate comprises an impermeable backing lamina, a scopolamine reservoir lamina, a release rate controlling lamina, an adhesive lamina and a release liner lamina and said dispersion forms said reservoir lamina.

6. The process of claim 5 wherein said dispersion forms said adhesive lamina.

7. The process of claim 6 wherein said subunits are heated to about 60° C. and held at that temperature for about 24 hours.

8. The process of claim 4 wherein said devices are heated to about 60° C. and held at that temperature for about 24 hours.

9. A process for preventing the formation of the crystalline hydrate of a liquid material dispersed within a non-aqueous matrix which comprises, in combination:
   a. forming a laminate, at least one lamina of which comprises a dispersion of a hydratable liquid in a matrix;
   b. cutting subunits from said laminate;
   c. packaging the individual subunits in sealed containers;
   d. heating said subunits in said packages to an elevated temperature and maintaining said subunits at said elevated temperature for a time sufficient to prevent the formation of said crystalline hydrate for a substantial period of time after cooling of the subunits to ambient temperatures; and
   e. cooling the subunits to ambient conditions.

10. The process of claim 9 wherein said liquid material is scopolamine base.

11. The process of claim 1 wherein said extended period of time is at least 6 months.

12. The process of claim 2 wherein said extended period of time is at least 6 months.

13. The process of claim 3 wherein said extended period of time is at least 6 months.

14. The process of claim 4 wherein said extended period of time is at least 6 months.

15. The process of claim 5 wherein said extended period of time is at least 6 months.

16. The process of claim 6 wherein said extended period of time is at least 6 months.

17. The process of claim 9 wherein said extended period of time is at least 6 months.

18. The process of claim 10 wherein said extended period of time is at least 6 months.

19. A process for producing laminated structure within a sealed container which comprises:
   a. forming a laminated structure, at least one lamina of which comprises a dispersion of a liquid capable of forming a crystalline hydrate in a nonaqueous matrix; and
   b. packaging said laminated structure in a sealed container;
   c. heating said laminated structure in said sealed container to an elevated temperature and maintaining said structure at said elevated temperature for a period of time sufficient to prevent formation of said crystalline hydrate for a substantial period of time after cooling of said laminated structure to ambient temperatures; and
   d. cooling said laminated structure in said sealed container to ambient temperatures.

20. In a process for producing a laminated structure within a sealed container which comprises:
   a. forming a laminated structure, at least one lamina of Which comprises a dispersion of a liquid capable of forming a crystalline hydrate in a nonaqueous matrix; and
   b. packaging said subunits in a sealed container; the improvement which comprises:
   c. heating said laminated structure in said sealed container to an elevated temperature;
   d. maintaining said structure at said elevated temperature for a period of time sufficient to prevent formation of said crystalline hydrate for a substantial period of time after cooling of said laminated structure to ambient temperatures; and
   e. cooling said laminated structure in said sealed container to ambient temperatures.

21. The process of claim 20 wherein said elevated temperature is above the melting point of said crystalline hydrate.

22. A process for producing a laminated dosage form of scopolamine packaged within a sealed container which comprises:
   a. forming a laminated dosage form of scopolamine, at least one lamina of which comprises a dispersion of a liquid scopolamine base in a nonaqueous matrix; and b. packaging said dosage form in a sealed container; the improvement which comprises:
c. heating said dosage form in said sealed container to an elevated temperature;

d. maintaining said dosage form at said elevated temperature for a period of time sufficient to prevent formation of a crystalline of scopolamine base for a substantial period of time after cooling of said dosage form to ambient temperatures; and e. cooling said dosage form in said sealed container to ambient temperatures.

23. The process of claim 22 wherein said elevated temperature is at least about 60° C.

24. The process of claim 23 wherein said time is about 24 hours.

* * * * *

UNITED STATES PATENT AND TRADEMARK OFFICE
CERTIFICATE OF CORRECTION

PATENT NO. : 4,832,953

DATED : 05/23/89

INVENTOR(S) : Patricia S. Campbell, David J. Enscore, Robert M. Gale, Arnold Kaufman It is certified that error appears in the above-identified patent and that said Letters Patent is hereby corrected as shown below:

Cover page, item [54] delete "MONAQUEOUS", insert --NONAQUEOUS--. Column 1, title, delete "MONAQUEOUS", insert --NONAQUEOUS--. Column 3, line 29, delete "udder", insert --under--; Column 3, line 32, delete "tee", insert --the--; Column 3, line 38, between present and If, insert --.--. Column 4, line 10, delete ".", insert --,--; Column 4, line 26, delete "pars", insert --parts--; Column 4, line 56, delete "laminate", insert --laminae--. Column 5, line 29, between "comprises" and "in", insert --,--. Column 6, line 45, delete "Which", insert --which--.

Signed and Sealed this

Twelfth Day of June, 1990

Attest:

HARRY F. MANBECK, JR.

*Attesting Officer*  *Commissioner of Patents and Trademarks*